(12) United States Patent
Tago et al.

(10) Patent No.: US 7,505,634 B2
(45) Date of Patent: Mar. 17, 2009

(54) RADIOGRAPHIC IMAGE PROCESSING APPARATUS, RADIOGRAPHIC IMAGE PROCESSING METHOD, COMPUTER PROGRAM, AND RECORDING MEDIUM THEREFOR

(75) Inventors: Akira Tago, Tokyo (JP); Tsukasa Sako, Kanagawa (JP); Koji Takekoshi, Kanagawa (JP)

(73) Assignee: Canon Kabushiki Kaisha, Tokyo (JP)

( * ) Notice: Subject to any disclaimer, the term of this patent is extended or adjusted under 35 U.S.C. 154(b) by 0 days.

(21) Appl. No.: 11/937,855

(22) Filed: Nov. 9, 2007

(65) Prior Publication Data

US 2008/0085045 A1 Apr. 10, 2008

Related U.S. Application Data

(63) Continuation of application No. 10/879,083, filed on Jun. 30, 2004, now Pat. No. 7,349,565.

(30) Foreign Application Priority Data

Jul. 3, 2003 (JP) ............... 2003-270649

(51) Int. Cl.
*G06K 9/36* (2006.01)
(52) U.S. Cl. .................... 382/284; 705/3
(58) Field of Classification Search ........ 703/3; 382/284
See application file for complete search history.

(56) References Cited

U.S. PATENT DOCUMENTS

| 5,826,237 | A | * | 10/1998 | Macrae et al. | 705/2 |
| 5,848,198 | A | * | 12/1998 | Penn | 382/276 |
| 6,567,121 | B1 | * | 5/2003 | Kuno | 348/211.3 |
| 6,789,087 | B1 | | 9/2004 | Sako | 707/104 |
| 6,836,558 | B2 | | 12/2004 | Doi et al. | 382/131 |
| 7,119,841 | B1 | | 10/2006 | Sako | 348/333.05 |
| 7,349,565 | B2 | * | 3/2008 | Tago et al. | 382/132 |
| 2002/0188475 | A1 | | 12/2002 | Banta et al. | 705/3 |
| 2004/0172292 | A1 | | 9/2004 | Takekoshi et al. | 705/2 |

FOREIGN PATENT DOCUMENTS

| JP | 03-287249 A | 12/1991 |
| JP | 06-327664 | 11/1994 |
| JP | 2000-232976 A | 8/2000 |

* cited by examiner

*Primary Examiner*—Matthew C Bella
*Assistant Examiner*—Dennis Rosario
(74) *Attorney, Agent, or Firm*—Fitzpatrick, Cella, Harper & Scinto

(57) ABSTRACT

In a radiographic image processing apparatus for generating synthesized image data by synthesizing a plurality of partial radiographic images generated by radiation that has passed through the same object, additional information added to each of the plurality of partial radiographic images is acquired. On the basis of the acquired additional information, it is determined whether synthesis is to be permitted. When it is determined that synthesis is not to be permitted, generation of the synthesized image data is inhibited.

19 Claims, 7 Drawing Sheets

RADIOGRAPHIC IMAGE PROCESSING APPARATUS, RADIOGRAPHIC IMAGE PROCESSING METHOD, COMPUTER PROGRAM, AND RECORDING MEDIUM THEREFOR

CROSS REFERENCE TO RELATED APPLICATION

This application is a continuation of Application No. 10/879,083, filed Jun. 30, 2004, and claims benefit of the filing date of that application, and priority benefit of the filing date of Japanese patent application no. 2003-270649, filed Jul. 3, 2003. The entire disclosures of the prior applications are incorporated herein by reference.

FIELD OF THE INVENTION

The present invention relates to a radiographic image processing apparatus and a radiographic image processing method, which process a radiographic image and, more particularly, to a radiographic image processing method and apparatus which are suitable for generating a whole image from a plurality of partial radiographic images generated from a common object portion.

BACKGROUND OF THE INVENTION

Conventionally, so-called diagnostic radiography is widely used to obtain internal information of patients, in which an image is acquired by using radiation (X-rays), and diagnosis is done. In conventional radiography, a film is set in a cassette together with a pair of intensifying screens (screen). Radiography is executed by using radiation, and the film is developed to obtain a radiographic image. Films used for this have standard sizes. Generally, so-called 14"×17" films are maximum and are popularly used.

For whole lower extremity radiography or whole spine radiography aiming at measuring a bone, a 14"×17" film is too small. Instead, a so-called long cassette is used, and radiography is executed by using a long film. However, a long film is difficult to process in development and the like. Alternatively, a plurality of 14"×17" films partially overlapping each other are set in a long cassette, and radiography is executed. In this case, after radiography, the films are developed one by one, and then, the plurality of films are bonded by tapes or the like to generate a whole image.

In recent years, apparatuses capable of acquiring a radiographic image directly as a digital image have been developed. In such an apparatus, a detector prepared by fixing stimulable phosphor to a sheet-shaped base plate by application or deposition is irradiated with radiation that has passed through an object so that the stimulable phosphor absorbs the radiation. When the stimulable phosphor is then excited by light or thermal energy, it radiates radiation energy accumulated in absorption as fluorescence. This fluorescence is photoelectrically converted to obtain an image signal.

When the above-described full spine radiography is to be executed by using this apparatus, radiography is executed by using a plurality of stimulable phosphor detectors partially overlapping each other. Then, the plurality of partial radiographic image data are synthesized to generate a whole image.

In, e.g., Japanese Patent Laid-Open No. 2000-232976, collateral information is attached to each partial radiographic image to indicate that the image is a part of a continuous radiographic image. By using the collateral information, synthesized image data is obtained from the partial radiographic images.

In the step of generating synthesized image data from a plurality of partial radiographic images, the plurality of partial radiographic images to be synthesized are designated. If wrong partial radiographic images are selected at this time, no correct synthesized image data can be obtained.

For example, a partial radiographic image of a wrong patient may be selected, or a partial radiographic image obtained in the past may be selected even though the patient is correct. In such a case, no correct synthesized image data can be obtained. In addition, wrong synthesized image data may lead to a wrong diagnosis.

SUMMARY OF THE INVENTION

The present invention has been made in consideration of the above problem, and has as its object to provide a radiographic image processing method which prevents generation of wrong synthesized image data when generating a whole image from a plurality of partial radiographic images.

According to the present invention, the foregoing object is attained by providing a radiographic image processing apparatus for generating synthesized image data by synthesizing a plurality of partial radiographic images generated by radiation that has passed through the same object, comprising:

acquisition means for acquiring additional information added to each of the plurality of partial radiographic images;

determination means for determining on the basis of the additional information acquired by the acquisition means whether synthesis is to be permitted; and inhibition means for inhibiting generation of the synthesized image data when the determination means determines that synthesis is not to be permitted.

In a preferred embodiment, the determination means determines whether synthesis is to be permitted by comparing each of the additional information added to the plurality of partial radiographic images.

In a preferred embodiment, the additional information is patient information of each of the plurality of partial radiographic images, and the determination means does not permit synthesis when each of the patient information added to the plurality of partial radiographic images do not coincide.

In a preferred embodiment, the additional information is information relating a radiographic apparatus which has radiographed the plurality of partial radiographic images, and the determination means does not permit synthesis when each of the information relating the radiographic apparatuses, which are added to the plurality of partial radiographic images, do not coincide.

In a preferred embodiment, the additional information is information relating a radiographic direction in which the plurality of partial radiographic images are radiographed, and the determination means does not permit synthesis when each of the information relating the radiographic directions, which are added to the plurality of partial radiographic images, do not coincide.

In a preferred embodiment, the additional information is information relating a pixel of the plurality of partial radiographic images, and the determination means does not permit synthesis when each of the information relating the pixels, which are added to the plurality of partial radiographic images, do not coincide.

In a preferred embodiment, the additional information is study information of the plurality of partial radiographic images, and the determination means does not permit synthesis when each of the study information added to the plurality of partial radiographic images do not coincide.

In a preferred embodiment, the additional information is radiography date/time information of the plurality of partial radiographic images, and the determination means does not permit synthesis when each of the radiography date/time information added to the plurality of partial radiographic images do not coincide.

In a preferred embodiment, the additional information includes study information and radiography date/time information of the plurality of partial radiographic images, and when each of the study information added to the plurality of partial radiographic images do not coincide, the determination means compares each of the radiography date/time information added to the plurality of partial radiographic images, and when each of the radiography date/time information do not coincide, the determination means does not permit synthesis.

In a preferred embodiment, each of the plurality of partial radiographic images has a plurality of kinds of additional information, and when at least two of the plurality of kinds of additional information do not coincide, the determination means does not permit synthesis.

In a preferred embodiment, the apparatus further comprises display means for displaying a window region to synthesize the plurality of partial radiographic images, and the inhibition means inhibits any partial radiographic image, for which the determination means determines that synthesis is not to be permitted, from being displayed on the window region.

In a preferred embodiment, when display on the window region is inhibited, the inhibition means executes warning display.

In a preferred embodiment, in the warning display, a factor which causes the determination means to inhibit synthesis is displayed.

In a preferred embodiment, when an operation of displaying a partial radiographic image on the window region is executed, the determination means determines whether synthesis of the partial radiographic image is to be permitted.

According to the present invention, the foregoing object is attained by providing a radiographic image processing method of generating synthesized image data by synthesizing a plurality of partial radiographic images generated by radiation that has passed through the same object, comprising:

an acquisition step of acquiring additional information added to each of the plurality of partial radiographic images;

a determination step of determining on the basis of the additional information acquired in the acquisition step whether synthesis is to be permitted; and an inhibition step of inhibiting generation of the synthesized image data when it is determined in the determination step that synthesis is not to be permitted.

According to the present invention, the foregoing object is attained by providing a computer program for generating synthesized image data by synthesizing a plurality of partial radiographic images generated by radiation that has passed through the same object, comprising:

acquisition processing for acquiring additional information added to each of the plurality of partial radiographic images;

determination processing for determining on the basis of the additional information acquired by the acquisition processing whether synthesis is to be permitted; and inhibition processing for inhibiting generation of the synthesized image data when it is determined by the determination processing that synthesis is not to be permitted.

Other features and advantages of the present invention will be apparent from the following description taken in conjunction with the accompanying drawings, in which like reference characters designate the same or similar parts throughout the figures thereof.

BRIEF DESCRIPTION OF THE DRAWINGS

The accompanying drawings, which are incorporated in and constitute a part of the specification, illustrate embodiments of the invention and, together with the description, serve to explain the principles of the invention.

DETAILED DESCRIPTION OF THE PREFERRED EMBODIMENT

A preferred embodiment of the present invention will be described in detail in accordance with the accompanying drawings.

Figure 1:
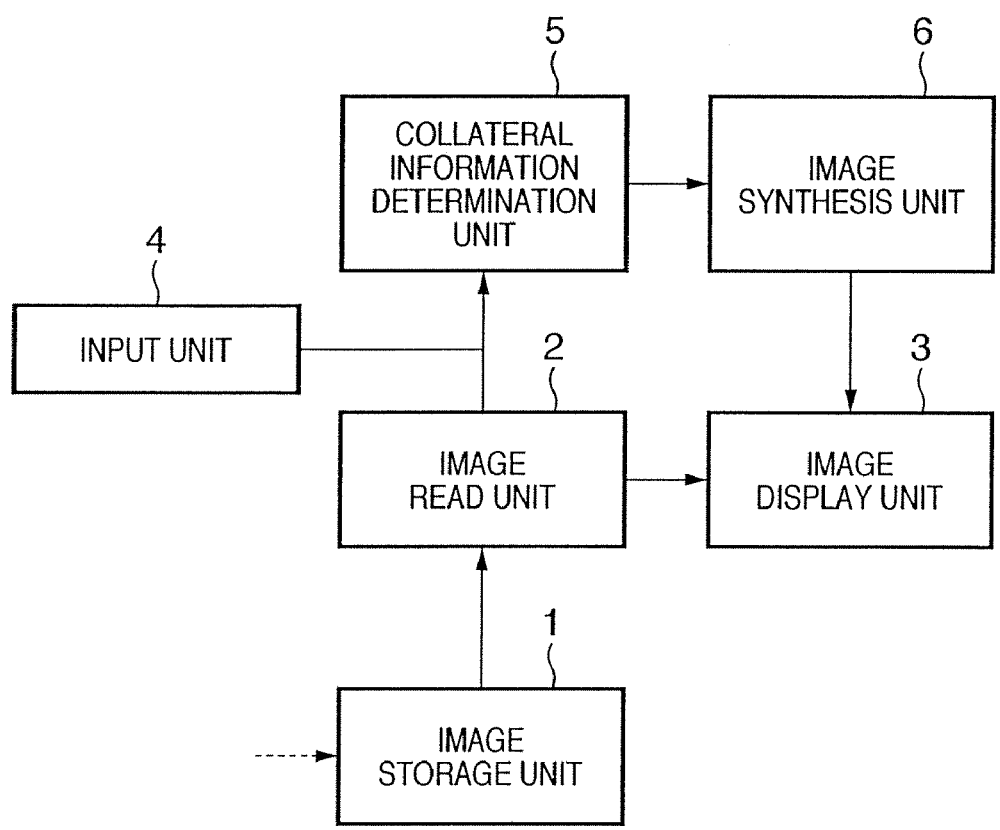
FIG. 1 is a block diagram showing the arrangement of the embodiment of the present invention.

FIG. 1 is a block diagram for explaining the arrangement of a radiographic image processing apparatus according to the embodiment of the present invention.

Referring to FIG. 1, an image storage unit 1 stores radiographic images as digital data. An image read unit 2 reads out radiographic image data from the image storage unit 1. The radiographic image data read out by the image read unit 2 is displayed on an image display unit 3.

The image display unit 3 includes, e.g., an LCD or CRT.

The image storage unit 1 stores digital data obtained by executing radiography by the screen-film method and reading, with a scanner, a radiographic image formed on a film by development, digital data obtained by executing radiography by using stimulable phosphor, data obtained by a flat sensor (so-called FPD) that combines a semiconductor element and phosphor, or digital data obtained by a semiconductor element sensitive to radiation.

The image storage unit 1 stores two partial radiographic images obtained by divisionally radiographing a whole spine from the front side, i.e., a first partial radiographic image for the upper spine including the cervical vertebra, and a second partial radiographic image for the lower spine including the lumbar vertebra. The first and second partial radiographic images generally overlap at the image synthesis portion.

An input unit 4 selects partial radiographic images to be synthesized from a plurality of radiographic images displayed on the image display unit 3. A collateral information determination unit 5 determines collateral information attached to partial radiographic images selected by the input unit 4. The collateral information determination unit 5 compares each of the collateral information of a plurality of partial radiographic images to be synthesized and determines whether synthesis of them is possible.

The input unit 4 includes, e.g., a keyboard, pointing device, or touch panel.

DICOM (Digital Imaging and Communications in Medicine) is widely used as a format of radiographic image data. This format includes image data and a DICOM header representing the collateral information of the image data. Patient ID information such as a patient name, patient ID, age, and sex, 7 radiography such as a study ID, study type, date/time of radiography, radiographed part, radiography conditions, and series ID, and information about image data such as the number of pixels, pixel size, and the number of bits are saved in the DICOM header.

When the collateral information determination unit 5 determines that the plurality of selected partial radiographic images should be synthesized, an image synthesis unit 6 synthesizes the images to generate a whole image. The synthesized image is displayed on the image display unit 3.

Figure 2:
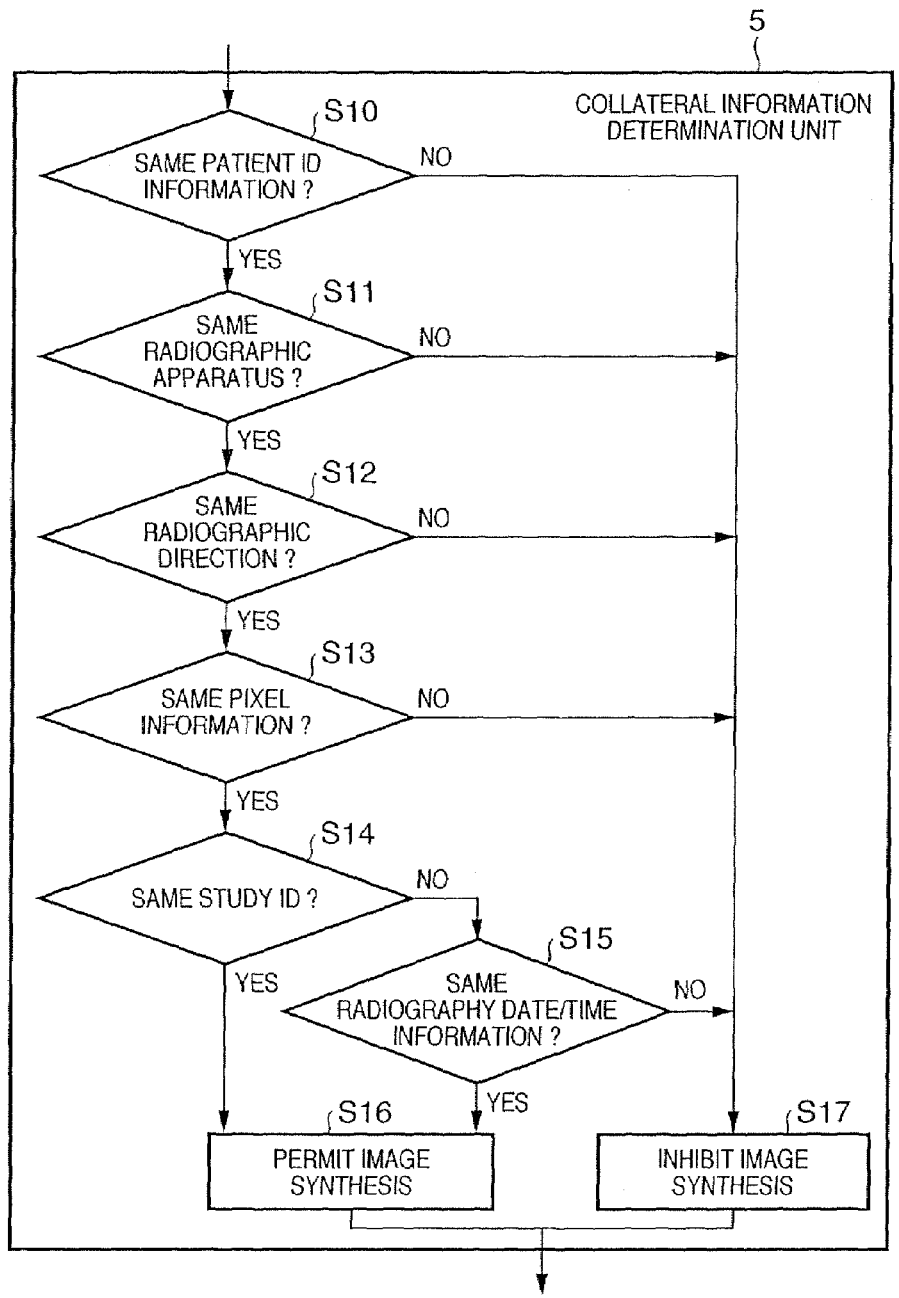
FIG. 2 is a flowchart of collateral information determination in the embodiment of the present invention.
Figure 3:
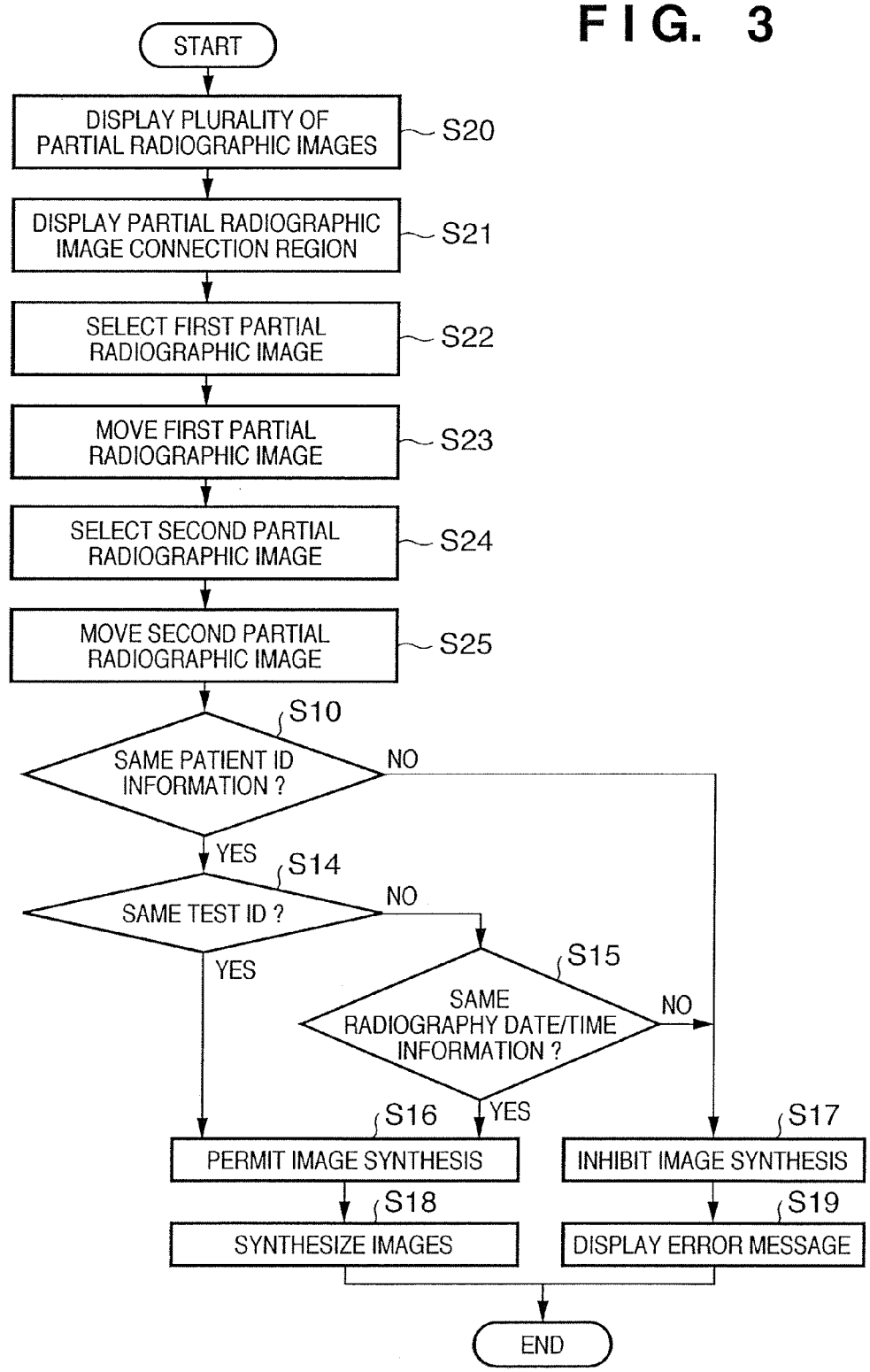
FIG. 3 is a flowchart of image synthesis in the embodiment of the present invention.

FIG. 2 shows details of the determination flow executed by the collateral information determination unit 5. DICOM headers attached to the first and second partial radiographic images selected by the input unit 4 are compared. It is determined on the basis of the comparison result whether the first and second partial radiographic images can be synthesized.

First, in step S10, the patient ID information of the first partial radiographic image, which is recorded on the DICOM header, is compared with that of the second partial radiographic image. If at least the patient names and patient IDs in the patient ID information do not coincide, the flow advances to step S17 to inhibit synthesis.

Since there may be persons of the same family and personal names, both the patient names and patient IDs are compared.

If the patient IDs coincide, the flow advances to step S11.

In step S11, each of the information about the radiographic apparatus such as its model name, which are recorded in the DICOM headers, are compared.

For example, a large scale hospital can have a plurality of radiographic apparatuses such as radiographic stands for a standing position and radiographic tables for a recumbent position. The positional relationship of internal organs changes between a radiographic stand for a standing position and a radiographic table for a recumbent position because of the gravity. For this reason, it is not preferable to synthesize an image radiographed on the radiographic stand for a standing position and an image radiographed on the radiographic table for a recumbent position.

The information relating the radiographic apparatus of the first partial radiographic image is compared with that of the second partial radiographic image. If each of the information do not coincide, the flow advances to step S17 to inhibit synthesis. If each of the information relating the radiographic apparatuses coincides, the flow advances to step S12.

In step S12, each of the information relating the radiographic directions, which are recorded in the DICOM headers, are compared. The information relating the radiographic direction of the first partial radiographic image is compared with that of the second partial radiographic image. If the radiographic directions of the two images do not coincide, the flow advances to step S17 to determine that image synthesis is inhibited. If the radiographic directions of the two images coincide, the flow advances to step S13.

Chest radiography is generally done in a direction in which radiation becomes incident from the back side and passes to the abdominal side (PA radiography). However, divided spine imaging is often done in a direction in which radiation becomes incident from the abdominal side and passes to the back side (PA radiography). This is because a blur-free image can be obtained by making the spine to be diagnosed closer to the sensor as much as possible. The distance between the sensor and the internal organs changes between a PA radiographic image and an AP radiographic image. Accordingly, the magnification also changes. It is not preferable to generate synthesized image data from images of different magnifications.

In step S13, each of the information relating the pixel sizes, which are recorded in the DICOM headers, are compared.

The resolution of a radiographic image to be obtained is determined by the sampling pitch (pixel size) in digitizing image information. The sampling pitch changes depending on the radiographic apparatus. There are various sizes such as 100 μm, 160 μm, and 200 μm. The information relating the pixel size contains the sampling pitch. When images with different pixel sizes are synthesized, a whole image that cannot exist is obtained.

To prevent this, the information relating the pixel size of the first partial radiographic image is compared with that of the second partial radiographic image. If each of the information relating the pixel sizes of the two images do not coincide, the flow advances to step S17 to determine that image synthesis is inhibited. If each of the information relating the pixel sizes of the two images coincide, the flow advances to step S14.

In step S14, each of the information relating the study IDs, which are recorded in the DICOM headers, are compared. Before radiography, a study ID is assigned to each study. A series of radiographic operations have the same study ID. For example, when a whole spine is radiographed divisionally in two parts, i.e., the upper and lower portions, the first partial radiographic image for the upper spine and the second partial radiographic image for the lower spine have the same study ID. The first and second partial radiographic images are discriminated by series numbers. Hence, the information relating the study ID of the first partial radiographic image is compared with that of the second partial radiographic image. If the two of information indicate the same study ID, the flow advances to step S16 to permit image synthesis.

If the two images have different study IDs, they are images radiographed in different studies. In this case, normally, it is determined that the images should not be synthesized, and image synthesis is inhibited. However, in radiographing a whole spine, the following situation often occurs. That is, an operation of radiographing a whole spine divisionally in two parts, i.e., the upper and lower portions is executed in a series of study procedures, and the same study ID is assigned. No problem is posed when the upper spine is radiographed, and continuously, the lower spine is radiographed. However, assume that the radiographer ends the study by misunderstanding after radiographing the upper spine. This can occur because chest radiography is generally done only once (i.e., divided radiography is not executed), and the two-divided radiography of a whole spine is rarely performed.

When the study is ended after obtaining the first partial radiographic image for the upper spine, a study ID different from that for the upper spine image is assigned to the second partial radiographic image for the lower spine. If the upper spine is radiographed once again with a new study ID, and the lower spine is continuously radiographed, two-divided radiography can be done with the same study ID. In this case, image synthesis is possible, though the radiation dose on the patient increases because the upper spine is radiographed twice.

In this embodiment, if the study IDs do not coincide, the flow advances to step S15 to compare the radiography date/time information recorded in the DICOM header of the first partial radiographic image with that of the second partial radiographic image.

The radiography date/time information of the first partial radiographic image is compared with that of the second partial radiographic image. If each of the information indicate that the images have been radiographed within a preset time (1 hr in this embodiment), the flow advances to step S16 to permit synthesis of the images. This is because even when the test is ended by mistake after radiographing the first image in divided radiography, radiography of the second image is prepared and executed within a short time. Accordingly, radiography need not be re-executed, and any increase in radiation dose on the patient can be prevented.

Detailed procedures of image synthesis will be described next with reference to FIGS. 3 and 4A to 4F.

Figure 4A:
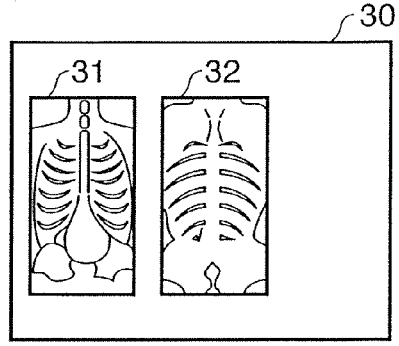
FIGS. 4A to 4F are explanatory views of image synthesis in the embodiment of the present invention.
Figure 4B:
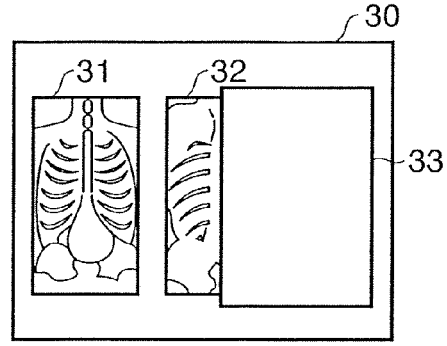

A plurality of partial radiographic images are displayed (step S20). Referring to FIG. 4A, reference numeral 30 denotes an image display portion of the display device (image display unit 3). A first partial radiographic image 31 as the upper radiographic image of a whole spine and a second partial radiographic image 32 as the lower radiographic image of the whole spine are displayed. A menu (not shown) is selected or a button is clicked on to display a partial radiographic image connection region 33, as shown in FIG. 4B (step S21).

A cursor (not shown) is moved onto the first partial radiographic image 31, and the left button of the mouse is clicked on to select the image (step S22). The first partial radiographic image 31 is copied to the partial radiographic image connection region 33 while keeping the left button of the mouse pressed (step S23).

Figure 4C:
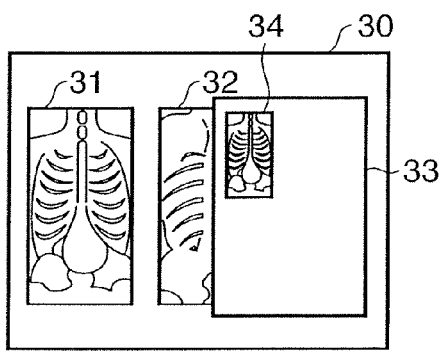

Accordingly, the first partial radiographic image 31 copied to the partial radiographic image connection region 33 is reduced to a predetermined size and displayed, as shown in FIG. 4C. Referring to FIG. 4C, reference numeral 34 denotes a reduced first partial radiographic image.

The cursor (not shown) is moved onto the second partial radiographic image 32, and the left button of the mouse is clicked on to select the image (step S24). The second partial radiographic image 32 is dragged into the partial radiographic image connection region 33 while keeping the left button of the mouse pressed (step S25).

Of the collateral information of the first partial radiographic image 31 and second partial radiographic image 32, each of the patient ID information are compared (step S10). If each of the patient ID information of the two images coincide, the flow advances to step S14. If each of the information do not coincide, the flow advances to step S17.

In step S14, of the collateral information of the first partial radiographic image 31 and second partial radiographic image 32, each of the study ID information are compared. If each of the study ID information of the two images coincide, it is determined that the selected first partial radiographic image 31 and second partial radiographic image 32 can be synthesized (step S16).

If each of the study ID information do not coincide in step S14, the flow advances to step S15. In step S15, of the collateral information of the first partial radiographic image 31 and second partial radiographic image 32, each of the radiography date/time information are compared. If the radiography dates/times of the two images fall within a preset time (1 hr in this embodiment), the flow advances to step S16 to permit synthesis of the images. If the radiography dates/times of the two images do not fall within the preset time, the flow advances to step S17.

Figure 4D:
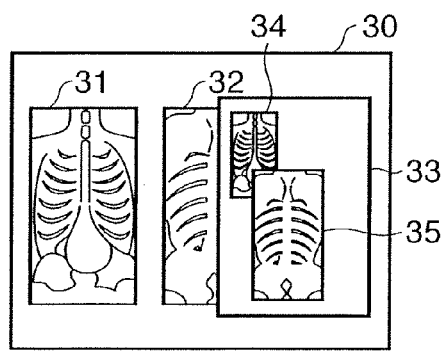

If the flow advances to step S16 to determine that the images can be synthesized, the second partial radiographic image 32 is copied to the partial radiographic image connection region 33. The second partial radiographic image 32 copied to the partial radiographic image connection region 33 is reduced to a predetermined size and displayed, as shown in FIG. 4D. Referring to FIG. 4D, reference numeral 35 denotes a reduced second partial radiographic image.

On the other hand, if the flow advances to step S17 to inhibit synthesis of the images, an error message 37 is displayed when the second partial radiographic image 32 is dragged into the partial radiographic image connection region 33. At this time, the second partial radiographic image 32 is not copied to the partial radiographic image connection region 33.

Figure 4E:
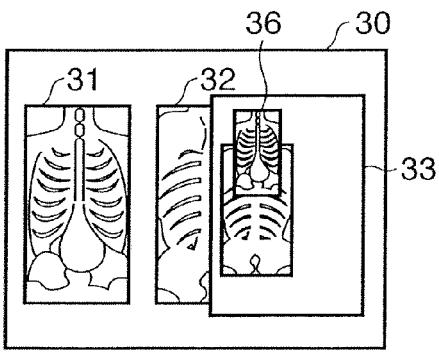
Figure 4F:
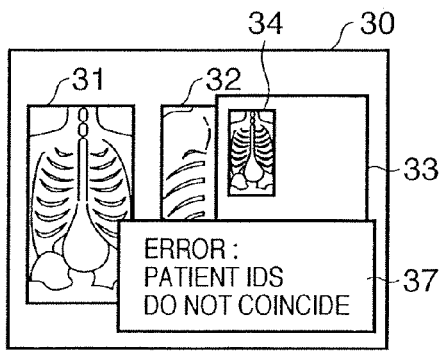

The error message 37 shown in FIG. 4F indicates that the patient ID information of the first partial radiographic image does not coincide with that of the second partial radiographic image. The display contents of the error message 37 change depending on conditions which do not coincide. That is, the error message 37 indicating the factor for inhibition of synthesis is displayed.

When image synthesis is permitted in step S16, the flow advances to step S18 so that an image synthesis operation can be executed.

FIG. 4E is a view for explaining the image synthesis operation in step S18.

Referring to FIG. 4E, the synthesis position between the reduced first partial radiographic image 34 and the reduced second partial radiographic image 35 is determined on the partial radiographic image connection region 33. In determining the synthesis position, the operator may move and position the first and second partial radiographic images such that they overlap at their common portion. Alternatively, the profiles of the images may be analyzed by a computer, and they may automatically be synthesized at the common portion of the profiles.

Figure 5:
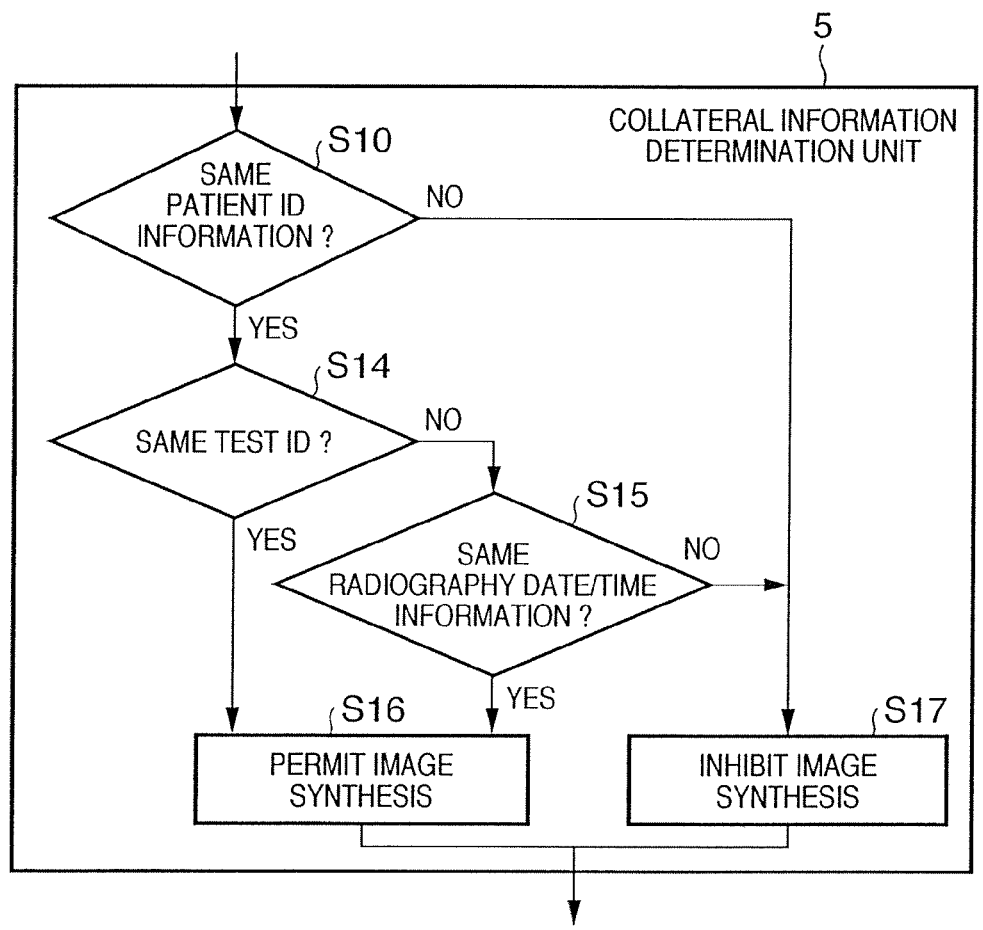
FIG. 5 is a flowchart showing a modification of collateral information determination in the embodiment of the present invention.

In this embodiment, the patient ID information, radiographic apparatus model name, radiographic direction, pixel size information, study ID, and radiography date/time information recorded in the DICOM header have been described as the collateral information to be compared. If there is only one radiographic apparatus, the radiographic apparatus model name and pixel size information need not be compared. The radiographic direction can also be omitted if any error in the direction can easily be recognized on the basis of the position of the heart. At this time, the collateral information determination unit 5 executes a determination flow shown in FIG. 5. The same step numbers as in FIG. 2 denote the same processes, and a description thereof will be omitted.

Figure 6:
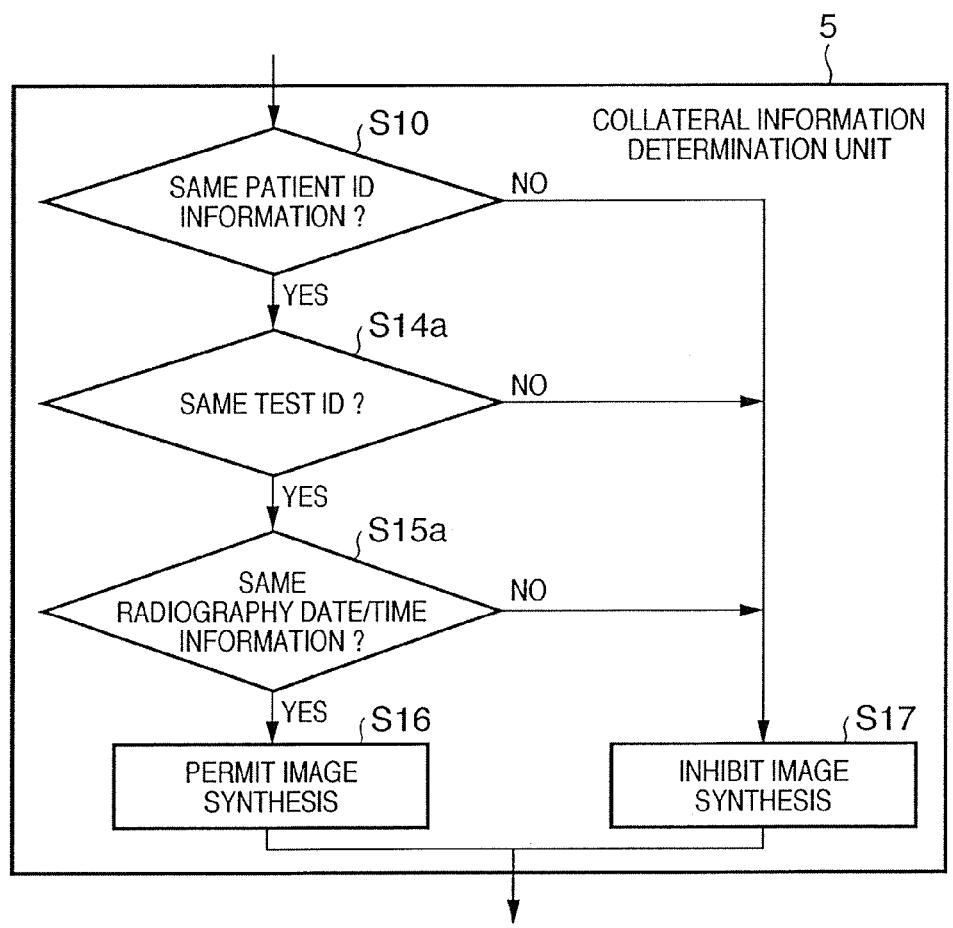
FIG. 6 is a flowchart showing another modification of collateral information determination in the embodiment of the present invention.

FIG. 6 shows a determination flow so as to explain a modification that uses the patient ID information, study ID, and radiography date/time information recorded in the DICOM header as collateral information to be compared. The same step numbers as in the embodiment shown in FIG. 2 denote the same parts, and a description thereof will be omitted.

First, in step S10, the patient ID information of the first partial radiographic image, which is recorded on the DICOM header, is compared with that of the second partial radiographic image. If at least the patient names and patient IDs in the patient ID information do not coincide, the flow advances to step S17 to inhibit synthesis. Since there may be persons of the same family and personal names, both the patient names and patient IDs are compared. If the patient IDs of the two images coincide, the flow advances to step S14a.

In step S14a, each of the information relating the study IDs, which are recorded in the DICOM headers, are compared. Before radiography, a study ID is assigned to each test. A series of radiographic operations have the same test ID. The information relating the study ID of the first partial radiographic image is compared with that of the second partial radiographic image. If the two images do not have the same study ID, the flow advances to step S17 to inhibit image synthesis. If the study IDs of the two images coincide, the flow advances to step S15a.

In step S15a, the radiography date/time information recorded in the DICOM header of the first partial radiographic image is compared with that of the second partial radiographic image. The radiography date/time information of the first partial radiographic image is compared with that of the second partial radiographic image. If the images have been radiographed within a preset time (1 hr in this embodiment), the flow advances to step S16 to permit synthesis of the images.

In this embodiment, image synthesis of the first and second partial radiographic images which are obtained by two-divided radiography has been described. However, the present invention can also be applied to synthesis of three or more partial radiographic images obtained by three-or-more divided radiography, as in whole lower extremity radiography.

As described above, according to this embodiment, a radiographic image processing apparatus for generating synthesized image data by synthesizing a plurality of partial radiographic images generated by radiation that has passed through the same object comprises acquisition means for acquiring additional information added to each of the plurality of partial radiographic images, determination means for determining on the basis of the additional information acquired by the acquisition means whether synthesis is to be permitted, and inhibition means for inhibiting generation of the synthesized image data when the determination means determines that synthesis is not to be permitted. With this arrangement, any image synthesis error can be prevented.

The determination means determines whether synthesis is to be permitted by comparing each of the additional information added to the plurality of partial radiographic images. Accordingly, it can easily be determined whether the plurality of partial radiographic images are appropriate for synthesis.

Each of the plurality of partial radiographic images has a plurality of kinds of collateral information. When at least two of the plurality of kinds of collateral information do not coincide, synthesis is inhibited. Hence, the determination means can reliably determine whether the plurality of partial radiographic images are appropriate for synthesis.

The apparatus further comprises display means for displaying a window region to synthesize the plurality of partial radiographic images. The inhibition means inhibits any partial radiographic image, for which the determination means determines that synthesis is to be inhibited, from being displayed on the window region. With this arrangement, the operator can clearly know that the synthesis operation for the partial radiographic image is inhibited and avoid wasteful synthesis operation.

When an operation of displaying a partial radiographic image on the window region is executed, the determination means determines whether synthesis of the partial radiographic image is to be permitted. Hence, determination can be done at an appropriate timing.

The object of the present invention can also be achieved by supplying a recording medium which stores software program codes for implementing the functions of the radiographic image processing apparatus of the embodiment to a system or apparatus and causing the computer (or CPU or MPU) of the system or apparatus to read out and execute the program codes stored in the recording medium.

In this case, the program codes read out from the recording medium implement the functions of the embodiment by themselves, and the recording medium which stores the program codes constitutes the present invention. As the recording medium for supplying the program codes, for example, a ROM, flexible disk, hard disk, optical disk, magnetooptical disk, CD-ROM, CD-R, magnetic tape, nonvolatile memory card, or the like can be used.

The functions of the embodiment are implemented not only when the readout program codes are executed by the computer but also when the OS running on the computer performs part or all of actual processing on the basis of the instructions of the program codes. The functions of the embodiment are also implemented when the program codes read out from the recording medium are written in the memory of a function expansion board inserted into the computer or a function expansion unit connected to the computer, and the CPU of the function expansion board or function expansion unit performs part or all of actual processing on the basis of the instructions of the program codes.

Figure 7:
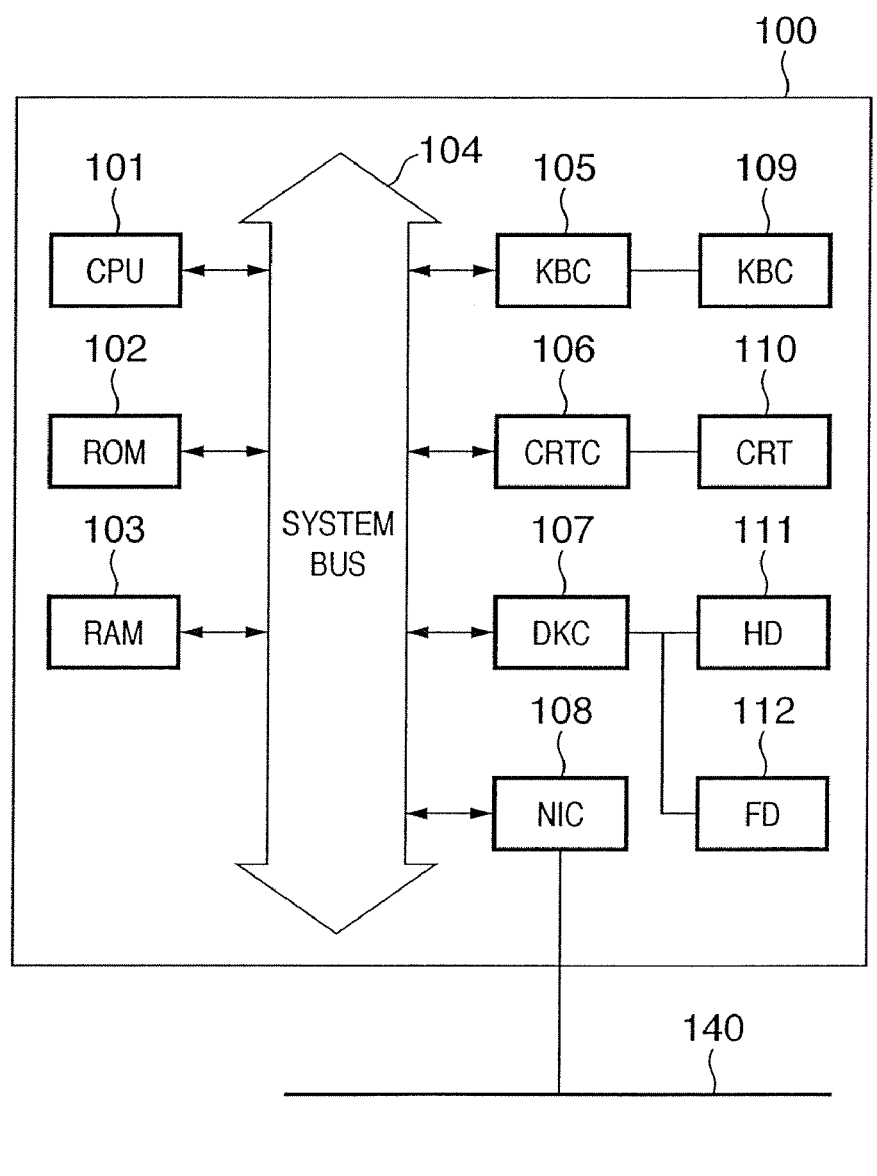
FIG. 7 is a block diagram for explaining the arrangement of a computer device according to the embodiment of the present invention.

FIG. 7 shows the arrangement of a computer function 100. As shown in FIG. 7, in the computer function 100, a CPU 101, a ROM 102, a RAM 103, a keyboard controller (KBC) 105 of a keyboard (KB) 109, a CRT controller (CRTC) 106 of a CRT monitor (CRT) 110 serving as a display unit, a disk controller (DKC) 107 of a hard disk (HD) 111 and flexible disk (FD) 112, and a network interface card (NIC) 108 for connection of a network 140 are connected via a system bus 104 to be communicable with each other.

The CPU 101 systematically controls the components connected to the system bus 104 by executing software stored in the ROM 102 or HD 111 or software supplied from the FD 112. More specifically, the CPU 101 executes control to implement the operation of the above embodiment by reading out a processing program corresponding to a predetermined processing sequence from the ROM 102, HD 111, or FD 112 and executing the program.

The RAM 103 functions as a main memory or work area of the CPU 101. The KBC 105 controls instruction input from the KB 109 or a pointing device (not shown). The CRTC 106 controls display of the CRT 110. The DKC 107 controls access to the HD 111 and FD 112 which store boot programs, various applications, editing files, user files, network management programs, and a predetermined processing program in the above embodiment. The NIC 108 bidirectionally transmits/receives data to/from another apparatus or system on the network 140.

The present invention is not limited to the above embodiments and various changes and modifications can be made within the spirit and scope of the present invention. Therefore, to apprise the public of the scope of the present invention, the following claims are made.

What is claimed is:

1. A radiographic image processing apparatus for generating a synthesized image by synthesizing a first radiographic image and a second radiographic image generated by radiation that has passed through the same object, comprising:
   acquisition means for acquiring patient information added to each of the first radiographic image and the second radiographic image;

first display means for displaying the first radiographic image when it is instructed that the first radiographic image is used for the synthesis;

determination means for determining, on the basis of the patient information acquired by said acquisition means, whether the synthesis is permitted or not when it is instructed that the second radiographic image is used for the synthesis after it is instructed that the first radiographic image is used for the synthesis; and second display means for displaying the second radiographic image synthesized with the first radiographic image when the determination means determines that the synthesis is permitted, and displaying an error message when the determination means determines that the synthesis is not permitted.

2. The apparatus according to claim 1, wherein the patient information is information relating to a radiographic apparatus that made the first radiographic image and the second radiographic image, and said determination means does not permit the synthesis when the information relating to the radiographic apparatus, which is added to the first radiographic image, and the information relating to the radiographic apparatus, which is added to the second radiographic image, do not coincide.

3. The apparatus according to claim 1, wherein the patient information is information relating to a radiographic direction in which the first radiographic image and the second radiographic image are radiographed, and said determination means does not permit the synthesis when the patient information relating to the radiographic direction, which is added to the first radiographic image, and the information relating to the radiographic direction, which is added to the second radiographic image, do not coincide.

4. The apparatus according to claim 1, wherein the patient information is information relating to a pixel of the first radiographic image and the second radiographic image, and said determination means does not permit the synthesis when the patient information relating to the pixel, which is added to the first radiographic image, and the information relating to the pixel, which is added to the second radiographic image, do not coincide.

5. The apparatus according to claim 1, wherein the patient information relates to study information of the first radiographic image and the second radiographic image, and said determination means does not permit the synthesis when the patient information added to the first radiographic image and the patient information added to the second radiographic image do not coincide.

6. The apparatus according to claim 1, wherein the patient information relates to radiography date/time information of the first radiographic image and the second radiographic image, and said determination means does not permit the synthesis when the radiography date/time information added to the first radiographic image and the information added to the second radiographic image do not coincide.

7. The apparatus according to claim 1, wherein the first radiographic image and the second radiographic image has each have a plurality of kinds of additional information including patient information, and when at least two of said plurality of kinds of additional information do not coincide, said determination means does not permit the synthesis.

8. The apparatus according to claim 7, wherein said second display means changes the display of the error message according to the kinds of patients information that do not coincide.

9. The apparatus according to claim 1, wherein said first display means displays the first radiographic image reduced to a predetermined size when it is instructed that the first radiographic image is used for the synthesis, and said second display means displays the second radiographic image reduced to a predetermined size synthesized with the first radiographic image reduced to a predetermined size when the determination means determines permits the synthesis.

10. A radiographic image processing method of generating synthesized image by synthesizing a first radiographic image and a second radiographic image generated by radiation that has passed through the same object, comprising:

an acquisition step of acquiring patient information added to each of the first radiographic image and the second radiographic image;

a first display step of displaying, on a display, the first radiographic image when it is instructed that the first radiographic image is used for the synthesis;

a determination step of determining, on the basis of the patient information acquired in said acquisition step, whether the synthesis is permitted or not when it is instructed that the second radiographic image is used for the synthesis after it is instructed that the first radiographic image is used for the synthesis; and a second display step of displaying, on the display, the second radiographic image synthesized with the first radiographic image when it is determined in the determination step that the synthesis is permitted, and displaying an error message when it is determined in the determination step that the synthesis is not permitted.

11. The method according to claim 10, wherein the patient information is information relating to a radiographic apparatus that made the first radiographic image and the second radiographic image, and in the determination step, the synthesis is not permitted when the information relating to the radiographic apparatus, which is added to the first radiographic image, and the information relating to the radiographic apparatus, which is added to the second radiographic image, do not coincide.

12. The method according to claim 10, wherein the patient information is information relating to a radiographic direction in which the first radiographic image and the second radiographic image are radiographed, and in the determination step, the synthesis is not permitted when the patient information relating to the radiographic direction, which is added to the first radiographic image, and the information relating to the radiographic direction, which is added to the second radiographic image, do not coincide.

13. The method according to claim 10, wherein the patient information is information relating to a pixel of the first radiographic image and the second radiographic image, and in the determination step, the synthesis is not permitted when the patient information relating to the pixel, which is added to the first radiographic image, and the information relating to the pixel, which is added to the second radiographic image, do not coincide.

14. The method according to claim 10, wherein the patient information relates to study information of the first radiographic image and the second radiographic image, and in the determination step, synthesis is not permitted when the study information added to the first radiographic image and the study information added to the second radiographic image do not coincide.

15. The method according to claim 10, wherein the patient information relates to radiography date/time information of the first radiographic image and the second radiographic image, and in the determination step, the synthesis is not permitted when said determination means does not permit the synthesis when the radiography date/time information added to the first radiographic image and the information added to the second radiographic image do not coincide.

16. The method according to claim 10, wherein the first radiographic image and the second radiographic image each have a plurality of kinds of additional information including patient information, and in the determination step, when at least two of the plurality of kinds of additional information do not coincide, the synthesis is not permitted.

17. The method according to claim 16, wherein, in the second display step, the display of the error message is changed according to the kinds of patient information that do not coincide.

18. The method according to claim 10, wherein, in the first display step, the first radiographic image is displayed reduced to a predetermined size when it is instructed that the first radiographic image is used for the synthesis, and in the second display step. the second radiographic image is displayed reduced to a predetermined size synthesized with the first radiographic image reduced to a predetermined size when it is determined in the determination step that the synthesis is permitted.

19. A computer-readable recording medium storing, in executable form, a computer program for generating synthesized image by synthesizing a first radiographic image and a second graphic image generated by radiation that has passed through the same object, comprising:

acquisition processing for acquiring patient information added to each of the first radiographic image and the second radiographic image;

first display processing for displaying the first radiographic image when it is instructed that the first radiographic image is used for the synthesis;

determination processing for determining, on the basis of the patient information acquired by said acquisition processing, whether the synthesis is permitted or not when it is instructed that the second radiographic image is used for the synthesis after it is instructed that the first radiographic image is used for the synthesis; and second display processing for displaying the second radiographic image synthesized with the first radiographic image when the determination processing determines that the synthesis is permitted. and displaying an error message when the determination processing determines that the synthesis is not permitted.

* * * * *